United States Patent [19]

Phillips

[11] Patent Number: 4,734,360
[45] Date of Patent: Mar. 29, 1988

[54] COLORIMETRIC ETHANOL ANALYSIS METHOD AND TEST DEVICE

[75] Inventor: Roger C. Phillips, Palo Alto, Calif.

[73] Assignee: Lifescan, Inc., Mt. View, Calif.

[21] Appl. No.: 624,774

[22] Filed: Jun. 26, 1984

Related U.S. Application Data

[63] Continuation-in-part of Ser. No. 513,505, Jul. 12, 1983, abandoned.

[51] Int. Cl.$^4$ .......................... C12Q 1/26; C12Q 1/28; C12N 9/96
[52] U.S. Cl. ........................ 435/25; 435/28; 435/188; 435/805
[58] Field of Search ............... 435/4, 25, 28, 188, 435/189, 805, 810; 436/169, 170, 175, 176; 422/56, 57

[56] References Cited

U.S. PATENT DOCUMENTS

| 3,413,198 | 11/1968 | Deutsch | 435/4 X |
|---|---|---|---|
| 3,926,736 | 12/1975 | Bucolo | 435/26 |
| 3,992,158 | 11/1976 | Przybylowica et al. | 435/11 X |
| 4,076,502 | 2/1978 | Dugle et al. | 435/14 |
| 4,427,632 | 1/1984 | Okaniwa et al. | 435/14 X |
| 4,430,427 | 2/1984 | Hopkins | 435/25 |
| 4,450,153 | 5/1984 | Hopkins | 424/94 |
| 4,642,286 | 2/1987 | Moldowan | 435/25 |

OTHER PUBLICATIONS

Janssen et al, *Biochimica et Biophysica Acta,* vol. 151, 330–342, 1968.

Majkic–Singh et al, *Analytica Chimica Acta,* vol. 115, 401–405, 1980.

*Primary Examiner*—Alvin E. Tanenholtz
*Assistant Examiner*—Jayme A. Huleatt
*Attorney, Agent, or Firm*—Leydig, Volt & Mayer

[57] ABSTRACT

A disposable test strip device for detecting and measuring ethanol in aqueous solutions is disclosed. The test strip includes an inert support pad that contains a stabilized dry form of the enzyme alcohol oxidase, a material having peroxidative activity and an oxygen acceptor that reacts with hydrogen peroxide to give a compound of changed color. The use of this strip to determine ethanol levels colorimetrically is also disclosed.

4 Claims, 4 Drawing Figures

COLORIMETRIC ETHANOL ANALYSIS METHOD AND TEST DEVICE

This application is a continuation-in-part of application Ser. No. 513,505, now abandoned, filed July 12, 1983.

FIELD OF THE INVENTION

This invention is in the field of enzyme-mediated colorimetric analysis. It concerns a colorimetric analysis method and test device for determining low concentrations of ethanol in aqueous media, particularly in human body fluids.

BACKGROUND OF THE INVENTION

There is an increasing demand for a simple but accurate and reproducible method for determining relatively low concentrations e.g., 0.025, 0.05, 0.10 or 0.20% of ethanol in aqueous fluids. One common application of such a method could be to measure ethanol levels in human body fluids as a test for highway intoxication or sobriety. Another would be to assure that operators of dangerous equipment, such as heavy construction equipment or military equipment are not intoxicated by alcohol. The chemical methods of choice for such tests include complex laboratory procedures such as gas chromatography for analyzing blood or urine, and a range of laboratory or field colorimetric tests. Since the late 1930's the "Drunkometer" of Stephenson Corporation has been in use. This colorimetric machine relies on the ability of ethanol in the breath to react with and discolor aqueous acidic potassium permanganate. In 1954 the Stephenson Corporation introduced the widely used "Breathalyzer" which relies on the decolorizing reaction of ethanol in the breath with acidic potassium dichromate to determine intoxication. These tests have a long history of use which has not been without difficulty and controversy. They require difficult to carry wet reagents, calibration and a reasonable level of operator competence to give good readings. They are not readily suited for rapid routine processing of large groups of samples.

Another application for the rapid determination of blood alcohol levels is in the hospital emergency rooms. Approximately ⅓ of all patients currently admitted to hospital emergency rooms are tested for blood alcohol level for the purpose of making a correct judgment as to the nature of their clinical condition. Since no simple rapid method has previously existed for such a measurement current practice is to take a blood sample by venipuncture and to hand carry it to the laboratory for a stat blood alcohol determination. This procedure takes from 30 minutes to a few hours.

The present invention employs the enzyme alcohol oxidase. This material was reported by Janssen et al in *Biochem Biophys Res Commun* (US) Sept. 8, 1965, 20, (5) p 630–4 and is presently sold by Boehringer Mannheim Biochemicals, Indianaoolis, IN and Phillips Chemical, a subsididary of Phillips Petroleum.

Alcohol oxidase is a particularly unstable enzyme undergoing rapid deterioration and loss of activity. It is sold by Phillips as a solution in 70% by weight sucrose. It is sold by Boehringer as a solid, stabilized with large amounts of the peroxide antagonist, reduced glutathione. This is not an acceptable form for this analysis which requires that hydrogen peroxide be generated and quantitated. The large amounts of peroxide antagonist would interfere with this. In addition, it has also been found that this enzyme has the interesting but difficult to deal with property of undergoing autoxidation, generating peroxide by reaction with itself.

This enzyme's use in electrode ethanol analysis systems has been reported in *Chem Abstracts*, 94, 135580a, and is mentioned in U.S. Pat. No. 4,250,261 of Eggeling et al. Majkic-Singh and Berkes reported at *Analytica Chemica Acta*, 115, 401–5 (1980) a method for determining ethanol in which the chromogen 2,2'-azino-di(3-ethylbenzthiazoline-6-sulfonate) (ABTS) was reacted with hydrogen peroxide generated by alcohol oxidase. This prior method is carried out measuring the absorbance of solutions in a spectrophotometer in a laboratory setting. It is also characterized by careful handling of the sensitive alcohol oxidase in an effort to prevent deterioration or variation of results.

U.S. Pat. No. 4,430,427 of Hopkins also employs ethanol oxidase in a solution analysis setting.

What is now sought and provided by the present invention is a long-lived accurate and precise simple colorimetric method for determining ethanol concentrations in aqueous fluids such as human body fluids, in particular saliva and whole blood.

STATEMENT OF THE INVENTION

A device and method for detecting and measuring the ethanol in aqueous solutions has now been found. The device is a disposable test strip which includes an inert support pad that contains a stabilized dry form of the enzyme alcohol oxidase, a material having peroxidative activity and an oxygen acceptor that reacts with hydrogen peroxide to give a compound of changed color.

When this device is contacted with an aqueous solution containing a measurable concentration of ethanol up to about 0.3% ethanol, at essentially ambient conditions, the ethanol reacts with oxygen and the alcohol oxidase to generate hydrogen peroxide ($H_2O_2$). The $H_2O_2$ reacts with the peroxidase and the oxygen acceptor to generate or consume colored compound in an amount proportional to the ethanol concentration. The amount of colored compound is determined by measuring the color intensity. Color intensity can be determined using reflectance measurement such as a reflectance spectrophotometer or by comparison with standards. Thus, the device and method find ready application in at least two general areas of use.

In another aspect this invention provides a stabilized form of alcohol oxidase "stabilized alcohol oxidase" which is employed in the above-noted test device and method. "Stabilized alcohol oxidase" can be achieved by intimately combining alcohol oxidase with a stabilizing concentration of a solid aliphatic polyhydroxyl compound having 5 to 8 carbons, and 5 to 7 hydroxyl groups, optionally with a saccharide and a chelating agent.

An additional and necessary aspect of this invention provides a neutralized form of alcohol oxidase in which the enzyme's tendency to autoxidize is eliminated or suppressed by admixture with a controlled amount of a peroxide scavenger such as ascorbic acid or cysteine.

In a further aspect, when this invention is employed to quantitate rather than qualitate ethanol, an additional controlled amount of a peroxide scavenger is admixed with the alcohol oxidase to give a more gradual color change.

DETAILED DESCRIPTION OF THE INVENTION

BRIEF DESCRIPTION OF THE DRAWINGS

The drawing contains four figures.

Figure 1:
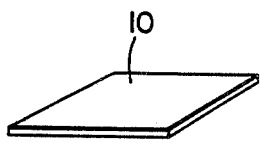
FIG. 1 is an enlarged, not to scale perspective view of a very simple embodiment of the device of this invention.

The test device of this invention, in a very simple form is shown in FIG. 1 as a pad 10 made up of a hydrophilic absorbent material which can absorb the sample of aqueous material to be tested for ethanol. The pad carries the enzyme systems and color-changing oxygen acceptor which react to generate the color change in response to ethanol. Pad 10 can be made of natural or synthetic absorptive materials. Pad 10 may be of any water-insoluble hydrophilic material including natural materials like cellulose, paper, cotton, silk, and cross-linked gelatin and synthetic materials such as cross-linked hydroxymethyacrylates and acrylates, cellulose acetate, cellulose nitrate, cross-linked poly(vinyl alcohol), poly(vinylamine), poly(vinylsulfonate) copolymers, poly(styrene sulfonate) and copolymers containing styrene sulfonate units, poly(vinyl acetate), poly(maleic anhydride), poly(vinyl 2-methoxyethyl ether), poly(4-vinyl phthalic acid), poly (N-vinylmorpholinone), poly(N-vinylpyrrolidone), poly(methacrylic acid), poly(acrylamide), poly(methacrylamide), poly(ethylene oxide) and the like. The hydrophilic material may be a gel layer, porous or fibrous, or the like. Cellulose and cellulose derivatives are readily available, work fine and thus are preferred hydrophilic substrates. An aqueous liquid sample is applied to pad 10. Substrate pad 10 is sized to be smaller in volume than the sample which is applied to it. If it is larger or similar in volume to the sample, there are problems with the sample pad "chromatographing" the sample or "spreading" the sample and giving an uneven result. As depicted in FIG. 1, pad 10 is not necessarily drawn to scale. Usually it is from about 0.01 mm to 0.5 mm thick, most commonly 0.05 to 0.30 mm thick.

In the application of this device to screen humans for intoxication, the aqueous sample is whole blood, saliva or urine. In the case of blood, a 5-20 microliter volume from a minimally traumatic "finger-prick" is very preferably used. Generally, when fresh whole blood is the sample being tested the test pad should be on the order of 10 mm$^2$ to 100 mm$^2$ in area, especially 10 mm$^2$ to 50 mm$^2$ in area. The sample pad contains the enzymes and chemical reagents which will react with any ethanol to produce a compound of changed color especially of an intense blue color. These will be described separately, below.

Figure 2:
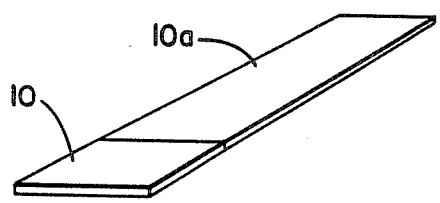
FIGS. 2, 3 and 4 likewise are enlarged not to scale views of somewhat more complex embodiments of the device of this invention.

Turning to FIG. 2 a second embodiment of the device of this invention is shown. In this embodiment, pad 10 as described, is affixed to handle 10a. Handle 10a can be the same material as pad 10, without the reagents or it can be a different material such as will be described as a backing with reference to FIG. 3.

Figure 3:
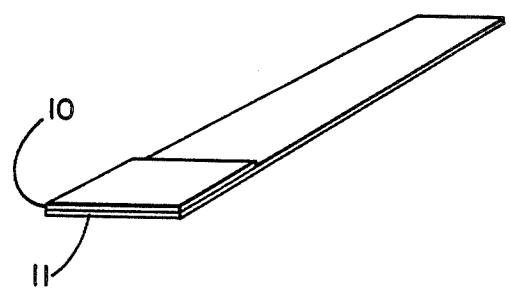

In FIG. 3, another embodiment of the device of this invention is shown to comprise absorbent pad 10 affixed to backing 11. Backing 11 is preferably of a material that does not absorb the aqueous sample. It can be made of plastic, wood, hydrophobic paper products such as water-repellant-treated board stock, heavy paper, or the like. In one special embodiment, backing 11 and pad 10 are chosen so that pad 10 is at least partially transparent or translucent and backing 11 presents a diffuse reflective surface. This configuration for a test device generally and its use with a diffuse reflectance meter is disclosed and claimed in commonly-assigned copending U.S. patent application Ser. No. 438,399 now abandoned.

Figure 4:
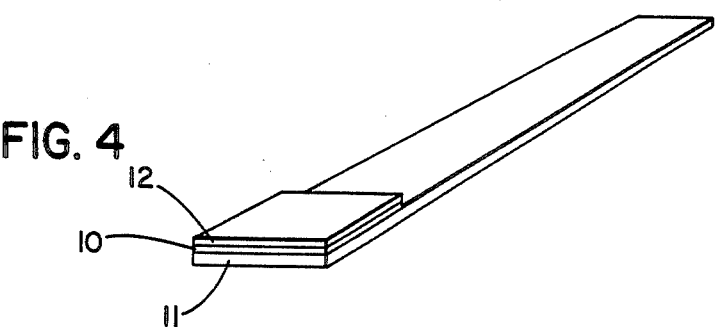

In FIG. 4, yet another embodiment of the present invention is shown in which pad 10 is overcoated with a semipermeable transparent "membrane" 12. This membrane is permeable to small molecules like water and ethanol but is impermeable to whole blood cells and similar large molecules. Such membranes are disclosed in the art of blood glucose measuring devices (See U.S. Pat. No. 4,211,845 of Genshaw and U.S. Pat. No. 3,298,789 of Mast). This is the preferred method for quantitation of ethanol in whole blood. Ethyl cellulose has been used in that application and works in the present case. Other equivalent materials such as cellulose acetate, cellulose proprionate, polyvinylacetate and polymethylmethacrylate can be employed, as well. This membrane is of advantage when alcohol levels are being detected in a fluid like blood which is colored by large bodies (i.e., whole blood cells). The membrane keeps the colored cells out of the reagent pad. Prior to determining the color change they can be washed or wiped away and thus do not interfere with the color change in the reagent pad.

FIG. 4's depiction of membrane 12 illustrates one possible form of such a membrane and makes it easy to see how the membrane works. However, in the most common embodiments this over-coating layer is applied to the pad as a solution or "varnish" in a water impermeable organic solvent like toluene, benzene or the like which is dried. Electron micrographs of materials formed in this manner reveal that the over-coating layer is not exactly the discrete unit of FIG. 4 but rather coats the individual fibers making up pad 10. Both embodiments work the same and are included within the definition of membrane 12.

Optionally, pad 10 including coating 12 is covered by a protective cover that is not shown. This cover is removed in use but is removably sealed around pad 11 prior to use. This cover can be made of foil, waterproofed paper, or water-oxygen and light-impermeable protective plastic such as poly(ethylene) or poly(vinylchloride) or the like and is provided to protect the enzymes and chemicals in pad 10 from degradation prior to the device's use in testing.

Pad 10 contains a reagent system. The reagent system is made up of stabilized alcohol oxidase, a peroxidase and a color-changing oxygen acceptor. It may contain other materials as well. "Stabilized alcohol oxidase" is defined to mean alcohol oxidase which retains at least 50% of its activity and preferably at least 70% of its activity when stored in dry form at 56° C. for 15 days. With preferred embodiments of this invention a "Stabilized alcohol oxidase" can be attained which retains at least 90% of its activity under these test conditions. The stabilized alcohol oxidase is an important aspect of this invention and in its simplest form comprises alcohol oxidase in intimate admixture with an effective stabilizing concentration of a solid aliphatic compound with 5 to 8 carbons and 5 to 7 hydroxyl groups. Preferably the stabilized alcohol oxidase is buffered to an essentially neutral pH and also includes a chelating agent, especially an amine polyacid. In addition, the stabilized alcohol oxidase optionally includes a saccharide.

The alcohol oxidase is commercially available from two sources, Boehringer Mannheim Biochemicals (BMB) and Phillips Chemical. Neither supplier, however, has been able to develop a form of the enzyme suitable for the applications described herein. BMB offers the enzyme in a dry form which is stabilized with high levels of reduced glutathione, a peroxide scavenger. This form of the enzyme cannot be used for analytical applications based on peroxide chemistry because the high levels of glutathione interfere. Phillips Chemical has not been able to develop a stable dry form of the enzyme and thus offers only solutions of the enzyme which are shipped and stored in a frozen state. These solutions, however, can be converted to a stable, dry form using the methods described herein. The amount of enzyme used is conventionally expressed in units of enzyme activity, i.e., 500 units etc. Commerical solutions, when fresh generally contain about 1000 units/ml.

The solid aliphatic polyhydroxyl compound employed in the stabilized alcohol oxidase has 5 to 8 carbons and 5 to 7 hydroxyls. Preferably it has 5 or 6 carbons. Also preferably it is nonhygroscopic. Preferred of these materials are the solid polyhydric alcohols (polyols) having from 5 to 8 carbons and 5 to 7 hydroxyl groups, preferably 5 or 6 carbons. Examples of such materials are mannitol, sorbitol, blucitol and inositol. Mannitol is the preferred polyhydric alcohol.

The chelating agent is a material that can form a chelate complex with metal ions. Amine polyacids such as, ethylenediamine tetraacetic acid (EDTA) or ethylenediamine pentacetic acid, propylene 1,3-diamine tetraacctic acid and the like and especially 2 to 4 carbon alkyl-polyamine polyacids containing from 2 to 3 amine groups and from 4 to 7 aliphatic acid groups, especially acetic acid groups, are preferred. EDTA is the most preferred chelating agent because of ready availability.

The stabilized alcohol oxidase also is preferably buffered to give a pH when dissolved in water that is in the range of 6 to 9, preferably 7 to 8. This can be accomplished by adding a buffering amount of an inert buffering material such as an alkali metal phosphate or pyrophosphate, an alkali metal salt of maleic acid or an imidazole to the mixture.

During development of this invention it was separately determined that 3-(N-morpholino) propane sulfonic acid "MOPS" marketed in the USA by Research Organics of Cleveland, Ohio is a particularly useful buffer component.

Optionally, the stabilized enzyme system additionally contains a saccharide. One commercial preparation of alcohol oxidase contains a substantial amount of sucrose. Other similar mono or di or tri saccharides may be added as well. These include galactose, fructose, maltose, cellobiose and raffinose, for example.

A stabilizing amount of polyhydroxyl compound is present with the alcohol oxidase. A "stabilizing amount" or "stabilizing concentration" is an amount sufficient to achieve a "stabilized alcohol oxidase" as that term is herein defined. In general, such amounts involve a weight excess of the polyhydroxyl compound over the alcohol oxidase. As a guide, usually from about 0.3 to 2.5 grams of polyhydroxyl compound per 1000 units of enzyme are employed, preferably 0.4 to 1.2 grams of poly hydroxyl compound/1000 units alcohol oxidase.

The amount of chelating agent generally ranges from about 2 to about 50 mg/1000 units with use levels of about 4 to about 25 mg/1000 units being preferred.

When the optional saccharide is present it is usually present in up to about a 2 fold weight excess, based on the poly (hydroxyl) compound. Mixtures of two or more of any of the families of materials can be used in the stabilized enzyme systems, if desired.

By way of example, Table I lists a group of representative stabilized enzyme systems useful in the present invention. These systems are expressed in parts by weight based on the weight of dry alcohol oxidase present in the dry chemical mixture in the finished device.

TABLE I

| | |
|---|---|
| Alcohol Oxidase | 1000 units |
| Poly hydroxyl compound | 300–2500 mg |
| Chelating agent | 2–50 mg |
| Buffer | to pH 6–9 |
| Alcohol Oxidase | 1000 units |
| Mannitol and/or Sorbitol | 400–2000 mg |
| Alkylpolyamine polyacid | 2–50 mg |
| Phosphate Buffer | to pH 7–8 |
| Alcohol Oxidase | 1000 units |
| Mannitol | 400–2000 mg |
| EDTA | 2–50 mg |
| Phosphate Buffer | to pH 7–8 |
| Alcohol Oxidase | 1000 units |
| Mannitol | 400–2000 mg |
| EDTA | 2–50 mg |
| Saccharide | 400–2000 mg |
| Buffer | to pH 7–8 |

It will be readily understood by those skilled in the art that one does not depart from the teachings of this invention by incorporating inert materials and the like into the stabilized enzyme system. Generally, however, the addition of other stabilizers is not required and in fact many other materials considered to stabilize enzymes are deleterious when added. For example, alkali metal thiosulfates, polyvinyl alcohol, glycerine, casein and bovine serum albumin, all possible stabilizers, in fact, are destabilizers with alcohol oxidase. While small amounts of these substances may be present in the compositions without departing from the spirit of this invention, it is preferred to exclude such amounts which would have a substantial deleterious effect on the function and goals of the present invention.

The reagent system includes a material having peroxidative activity. This material promotes the reaction of the $H_2O_2$, generated by the reaction of ethanol with $O_2$, with the color-changing oxygen acceptor. While, most commonly, enzymatic plant peroxidases such as horseradish peroxidase or potato peroxidase are preferred and employed, various other organic or inorganic materials having peroxidative activity can be employed. These are known to include organics such as some of the porphyrins, as well as inorganics such as ammonium or alkali metal iodides, alkali metal chromic sulfates, iron II ferrocyanide, ferrous chloride and iron sulfocyanate, and the like. The material having peroxidative activity promotes reaction of $H_2O_2$ with the color-changing oxygen acceptor. A suitable oxygen acceptor is one which undergoes a visually-detectable color change when converted from a reduced state to an oxidized state. A large number of such materials have been disclosed heretofore, primarily in the context of glucose analyses.

Benzidine has been used as an oxygen acceptor in glucose analyses, but has carcinogenicity problems. 3,3,5,5-tetraalkylbenzidine is suggested as an oxygen acceptor in glucose analysis by U.S. Pat. No. 4,211,845. U.S. Pat. No. 3,630,847 discloses a family of parahydroxyl or paraamino pyridines as color-forming oxygen acceptors. Ngo and Lenhoff *Anal Biochem,* 105, 389–97 (1980) disclose using dimethylaminobenzoic acid and 3-methylbenzothiazolinone, again in a glucose analysis setting. The text, *Clinical Chemistry* by Richterich, et al, John Wiley & Sons, at pages 366–367 discusses O-dianisidine, O-tolidine, the ammonium salt of 2,2'-azinodi-[3-ethylbenzthiazoline sulfonic acid-(6)], 3-methyl-2-benzothiazolinone hydrazone/N,N-dimethylaniline, and phenol/4-aminophenazone as oxygen acceptors in glucose analysis. It should be emphasized that such materials are merely representative. This invention is not limited to any one specific color-changing (i.e., color forming or color decreasing) oxygen acceptor system. In general, any system which will react with $H_2O_2$ and give a color change proportional to the quantity of $H_2O_2$ can be employed. The Ngo and Lenhoff color forming system is excellent, however. It has a high extinction coefficient—i.e., it is very intense—its blue color is very distinctive.

The amount of oxygen acceptor can vary and will in part depend upon the materials employed. As a rough rule of thumb, the amount of oxygen acceptor ranges from about 5 to about 1000 mg per 1000 units of alcohol oxidase, with amounts from 10 to about 400 mg/per 1000 units of alcohol oxidase being preferred.

In copending U.S. Ser. No. 438,399, now abandoned incorporated herein by reference, it is disclosed that a colorimetric analysis of the present general structure can be based on color endpoint or on the rate of change of color. In that application it is noted that the rate measurement method can often give more precise results. In the present invention, it is preferred to use endpoint measurements. This is because the rate can depend not only on the amount of ethanol present (i.e., the desired parameter) but also on the activity of the alcohol oxidase (a nondesired parameter). Rate measurements in general and the methods set forth in U.S. Ser. No. 438,399 now abandoned in particular can be used but are not preferred.

If the test device is employed to merely give a yes-no indication of ethanol presence, the identity and amount of color-changing materials and the enzyme stabilization system can be selected to give a very large and very rapid color change with the only issue being the development of a distinctly measurable ethanol-dependent color change endpoint.

As noted in the background, alcohol oxidase undergoes an autoxidation reaction even when stabilized. This means that the system can sometimes give false positive endpoints. This can be prevented by neutralizing the peroxide functionality arising from autoxidation by adding a controlled neutralizing amount of peroxide scavenger to the reagent mixture. Such materials include ascorbic acid, cysteine, reduced glutathione, and uric acid. A neutralizing amount is specifically defined to be from 0.2 to 12 $\mu$ moles and especially 4–8 $\mu$ moles per 1000 units of alcohol oxidase. Such additions will prevent false positives and will give rise to a distinctly measurable endpoint.

In the more common application, it is desired to not only identify the presence of ethanol but also to quantify the amount of ethanol present. In this setting, the degree of color change should be selected, based on reagents employed, concentrations, and the like to give a detectable variance of color change depending on test sample ethanol levels. In such a test after a suitable period for color change development the color is read and the concentration of ethanol determined based on the color change.

The degree of color change can be moderated by adding additional peroxide scavenger to the test device. This addition has the effect of giving more separation between color changes seen with different ethanol levels. In general, additions of 4 to 80 $\mu$ moles of scavenger per 1000 units of alcohol oxidase will work, 4 to 20 $\mu$ moles, and expressly 4 to 8 $\mu$ moles/1000 units giving less separation in color change between varied ethanol levels, but concurrently greater absolute sensitivity to low ethanol levels while additions at the higher end of this range, i.e., 20 to 80 $\mu$ moles, especially 40 to 80 $\mu$ moles/1000 units giving greater separation but lower absolute sensitivity.

The time for color change development when quantitating ethanol is usually from about 10 seconds to several minutes. Generally a value equal to at least 95% of the endpoint is achieved in that time range. Longer times may be used subject to the caution that ethanol is generally more volatile than the aqueous sample in which it is contained so that it may be necessary to cover or enclose the test device in use to prevent preferential evaporation of the ethanol analyte.

The degree of color change brought about by reaction of ethanol can be determined in several ways. Two manual methods include comparing the test sample with a blank and comparing a test sample with a series of standards, each depicting a given ethanol level until a match is made.

The color change can also be measured instrumentally using a spectrophotometer or the like, either by comparison of the test sample with a blank preferably after a time interval adequate to give substantial, i.e., 90+% of the total color change, or less preferably, measurement by measuring the change in the absorbance of the test sample between two or more points in time.

The instrumental measurement of color change can be carried out by reflectance or absorption measurements at a wavelength at which the color change can be detected. As noted above, if reflectance measurement is employed, one may use a device and/or test method as is disclosed in U.S. Ser. No. 438,399 now abandoned.

The samples tested with the invention are aqueous samples, commonly human aqueous body fluids such as whole blood, serum, plasma, saliva and the like. Whole blood and saliva are usual test samples. It is well documented that the alcohol levels of these fluids are related and that these levels are in turn directly related to the subject's degree of intoxication. See, for example, *Clin. Sci.* (England), 56, No. 3 283–286, 1979 and *Clin. Exp. Pharmacol. Physiol.* (England), 6, No. 1, 53–59, 1979. Urine can also be the test sample, although its alcohol level is dependent upon a variety of factors other than only the amount of alcohol consumed and thus is not as good a measure of intoxication.

When the sample being tested is saliva, urine or a like lightly colored material, the devices of any of FIGS. 1 through 4 can be used. When the sample is deeply colored whole blood or the like, it is preferred, but not required, to use a device as set forth in FIG. 4 in which there is a membrane that can exclude whole blood cells and prevent their interference with the measurement of the color change.

The test method of this invention, in its broadest sense, involves applying a sample to the test strip, allowing the color change to take place, measuring the degree or rate of color change and relating that measured quantity to the level of alcohol. The protocol for such a test can be as follows for a "membrane" strip with whole blood, for example:

1. Apply sample of fresh whole blood (10–30 microliters) to pad of test strip.
2. After 20–40 seconds, blot strip, wiping of red cells and removing excess sample. (Period should be constant.)
3. Wait 20–90 seconds for color change to develop. (Again, period should be relatively constant.)
4. Read color change manually or instrumentally.
5. Relate color reading to ethanol level via standard calibration factors or the like.

One could use this type of protocol with other samples when a membrane device is employed.

With a no membrane strip the magnitude of color change can often be greater or more pronounced because the sample fully saturates the pad and a larger amount of reaction may occur. With such devices, a typical test protocol can be as follows:

1. Apply sample of fresh test liquid to the pad of the test device in an amount that more than saturates the pad. (10 microliters or more.)
2. Blot off excess test liquid.
3. Allow color change to develop. (Usually about 95% of total change has occurred in 2 minutes with 99+% within 4 minutes. Best results will be obtained if evaporation is minimized.
4. Read color change.
5. Correlate color change to ethanol levels as above.

When a rate measurement method is employed this is generally best carried out in a spectrophotometer which can make readings at two or more points in time, measured from the time the sample is contacted with the pad, and from these readings calculate a rate of change and from that rate automatically provide a ethanol level. Such a device is more fully set out in incorporated U.S. Ser. No. 438,399 now abandoned.

The method of producing the test devices in its general sense involves forming a solution of the enzyme, peroxidatively-active material, stabilizers, and color-changing oxygen acceptors; applying it to the pad substrate in a reproducible amount and manner and evaporating the solvent to deposit the materials on the substrate. The usual solvent is selected from water and water in combination with water-miscible (i.e. polar) inert organic solvents such as DMF, THF, DMSO, acetone or other ketones, acetonitrile or the like. Obviously, alcohols should not be used. These organics are generally employed to help solubilize the color-changing oxygen acceptor compounds which often are marginally soluble in water alone. The concentration of the components in the make-up solution can vary from about 20 to about 500 and especially 50 to 300 units of alcohol oxidase per ml, with the other components being present in the proportions set forth. The solution is usually made up by mixing all the materials except the ethanol oxidase and adding that material last. Once mixed, it is usually best to use the solution promptly. The drying of the test devices is usually carried out at mild conditions such as 15–30° C. and a vacuum. Similarly, it is preferred to store the test devices in a cool dry environment, ideally without substantial contact with oxygen. Once used, however, the test strips are very stable, holding a constant color for two weeks or more. This is true whether or not the strips are in contact with air, moisture or moderately elevated temperatures.

The invention will be further depicted by the following examples and comparative experiments which illustrate the preparation and use of representative devices in the measurement of ethanol in aqueous fluids and compare these results with other devices not of the invention. These examples are provided only to illustrate the invention and are not to be construed as limiting its scope.

EXAMPLE I

A test device for determining ethanol concentrations in aqueous fluids was produced. The device used as its colorforming oxygen acceptor, a system similar to the system of Ngo and Lenhoff, *Anal Biochem*, 105, 389–97 (1980) using dimethylaminobenzoic acid (DMAB) and 3-methylbenzothiazolinone hydrazone (MBTH).

A first solution was prepared DMAB (72 mg) was mixed with 0.5 ml of acetonitrile and 1.0 ml of 0.4 molar disodium phosphate buffer. The buffer held the pH at a level that causes most of the DMAB to deprotonate and thus go into solution. Disodium EDTA (2.4 ml of a 10 mg/ml solution) was added followed by 4.1 ml of deionized $H_2O$ and 1500 mg of mannitol (essentially to saturation). The solution was warmed to dissolve the mannitol, cooled to room temperature, and 6 mg of ascorbic acid was added. The amount of ascorbic acid added to this system is important as it serves as a means for "calibrating" of the system. Larger amounts of ascorbic acid slow the system's color development while smaller amounts permit color to develop more rapidly. The pH of the solution was adjusted to 7.2 with NaOH. Horseradish peroxidase (10 mg) having an enzyme activity of 108 units/mg was then added with vigorous mixing. This solution was held temporarily. For long term storage, it is advantageous to minimize oxygen contact by degassing and/or $N_2$ blanketing.

A second solution was made up to contain 144 mg of MBTH in 8 ml of 50/50 water/acetonitrile. Its pH was adjusted to 7.2 with NaOH.

A solution of alcohol oxidase (1000 enzyme units/ml) in 70% sucrose water was obtained (Phillips Petroleum). The first two solutions were mixed in a ratio of 4 parts to 1 part by volume and cooled to about 4° C. 1 part by volume of the alcohol oxidase solution (~ 4° C.) was added.

The mixed solution contained:
6 mg/ml DMAB
3 mg/ml MBTH
2 mg/ml $Na_2EDTA$
0.03 M disodium phosphate
12.5% mannitol
14% sucrose
12% v acetonitrile
0.5 mg/ml ascorbic acid
0.83 mg/ml peroxidase
1700 units/ml of alcohol oxidase The mixture (1.0 ml) was spread on a glass plate and a 3 cm x 3 cm piece of Whatman #541 paper was gently laid on the mixture so as to minimize "wicking" of the solution and maximize the evenness of saturation. The saturated paper was turned over to saturate the opposite side, taken up from the plate, placed on another plate, and dried in a 100 mm Hg absolute pressure 20–22° C. vac oven for 30 minutes. It was then held for ~ 16 hours at 760 mm Hg and 20-22° C. in a sealed container with silica gel dessicant to remove last traces of liquid.

The treated paper was cut into 0.5 cm × 0.6 cm pieces which were affixed with 3M #465 double-sided clear adhesive to white polystyrene supports to give test devices. Alternatively, and preferably the paper could be affixed by softening the polysytrene surface with solvent (toluene) and adhering the paper to the softened plastic.

After stressing 12 days at 56° C., the paper thus prepared retains virtually all of its original color when developed with 100 mg/dl ethanol.

EXAMPLE II

The preparation of Example I was substantially repeated with one change. After drying the impregnated paper, the paper was over-coated with a 1.0% by weight solution of ethyl cellulose in toluene and then dried at 20-22° C. in vacuuo to give a micromolecule impermeable membrane coat.

After stressing 14 days at 56° C., the paper thus prepared retains most of its original color when developed with 100 mg/dl ethanol. When used with whole blood to determine said blood's ethanol level, this strip has the advantage of not permitting whole blood cells to enter the strip so that they may be wiped off the strip easily.

EXAMPLE III

The preparation of Example I was repeated twice with the following change. In the first repeat, instead of 0.5 mg/ml of ascorbic acid, 1.0 mg/ml was used. In the second repeat no ascorbic acid was present. The first strip was more moderated than the strip of Example I, being less sensitive to low levels of ethanol in test samples but giving better color separation between samples of differing ethanol level. The second sample containing no ascorbic acid was extremely sensitive but gave poorer separation between samples.

EXAMPLE IV

A test device for ethanol similar to Example I is prepared using a single oxygen accepting dye component, 6-Dimethylamino-4-hydroxy-2-napthalenesulfonic acid (DMAN) in place of DMAB and MBTH. The first solution is prepared as in Example I, with the omission of DMAB. The second solution is prepared as in Example I, with the substitution of DMAB for MBTH. When developed with aqueous ethanol, the prepared paper gives a color varying from tan at 0 mg/ml EtOH to golden orange-yellow at 200 mg/dl EtOH.

COMPARATIVE EXPERIMENTS

As a base line, Comparative Experiment H was run. This was a repeat of Example I without stabilizers being present. That is, the mannitol and EDTA were omitted. The sucrose in the commercial alcohol oxidase was present. After storage for 18 days at 37° C. the paper thus prepared lost 68% of its color when developed with 100 mg/dl of EtOH. This result is tabulated in the Table following Example V along with the results of other comparative experiments conducted with a number of art-taught enzyme stabilizer components.

COMPARATIVE EXPERIMENT A

The preparation of Example I was substantially repeated, except that EDTA was omitted, 2 mg/ml casien was incorporated, and 0.8 mg/ml ascorbic acid was used. Casien is known as an enzyme stabilizer. After storage for 18 days at 37° C., the paper thus prepared lost a substantial amount of color when developed with 100 mg/dl EtOH indicating that casien was ineffective and probably destructive by comparison with Experiment H.

COMPARATIVE EXPERIMENT B

The preparation of Example I was substantially repeated, except that mannitol was excluded and 0.3 M tri(hydroxymethyl)aminomethane (TRIS) buffer was used in place of phosphate buffer. (TRIS) is suggested as an enzyme stabilizer but with alcohol oxidase was ineffective or even destructive.

COMPARATIVE EXPERIMENT C

The preparation of Example I was substantially repeated, except that mannitol was excluded and 20 mg/ml bovine serum albumin (BSA), an art taught enzyme stabilizer, was incorporated. No positive effect was observed and the product was less stable than unstabilized enzyme.

COMPARATIVE EXPERIMENT D

The preparation of Example I was substantially repeated, except that mannitol was excluded, and 30 mg/ml polyvinyl alcohol (PVA) was incorporated. Polyvinyl alcohol, a large molecule polyol not in accord with this invention destroyed the alcohol oxidase's activity. Another enzyme stabilizer is the three carbon polyol glycerol. This material is a liquid so not useful in a dry test strip and also has the property of reacting with alcohol oxidase and forming gels. Thus it is not useful.

COMPARATIVE EXPERIMENT E

The preparation of Example I was substantially repeated, except that mannitol was excluded, 0.4 M imidazole was substituted for phosphate buffer, and 25 mg/ml acacia, an art taught stabilizer was incorporated. Some stabilization was noted by comparison to Experiment H but its loss was many times that observed in Example I.

COMPARATIVE EXPERIMENT F

The preparation of Example I was repeated with the change that the pH was buffered to pH 5.5, a pH outside the range preferred herein. The enzyme was unstable at pH 5.5 and essentially all color forming ability was lost.

COMPARATIVE EXPERIMENT G

The preparation of Example I was repeated except that the EDTA was omitted and $Na_2S_2O_4$, an art-taught enzyme stabilizer, was added. The $Na_2S_2O_4$ did not work with alcohol oxidase—instead destroying the enzyme's activity.

EXAMPLE V

A series of test devices were prepared following the procedure of Example I. The ETDA, mannitol, buffer stabilizer system of Example I was replaced with a range of other stabilizers, and the pH was varied. The test devices were then stored for 14 to 20 days and their activity was determined by measuring their response to a standard 0.1% ethanol in water mixture. The formulations and results of the tests are given in the following table.

TABLE

| Sample | Stabilizer | Days of 37° C. Stress | % Color Retained |
| --- | --- | --- | --- |
| Example I | 0.2% EDTA, 10% mannitol, pH 7.2 | 17 | 100 |
| Example Va | 0.05% Cysteine, 10% mannitol, pH 7-8 | 19 | 100 |
| Example Vb | 0.02% Sodium Azide, 10% mannitol | 17 | 86 |
| Example Vc | pH 7.2 phosphate buffer, 10% mannitol | 16 | 90 |
| Example Vd | pH 9.0 phosphate buffer, 10% mannitol | 16 | 90 |
| Comparative Experiment | | | |
| A | casien added, EDTA omitted | 18 | <30 |
| B | Tris added, phosphate omitted mannitol omitted | 18 | 7 |
| C | BSA added, mannitol omitted | 18 | 24 |
| D | PVA added, mannitol omitted | 17 | 1 |
| E | Imidazole added, acacia added, mannitol omitted | 17 | 51 |
| F | 0.2% EDTA, 10% mannitol, pH 5.5 | 16 | 3 |
| G | $Na_2S_2O_4$ added, EDTA omitted | 14 | 0 |
| H | No stabilizer | 18 | 32 |

EXAMPLE VI

An additional test device employing this invention was prepared. A first solution was prepared by dissolving 9.64 g of anhydrous MBTH.HCl, 5.03 g an anhydrous MOPS and 30.6 g of sucrose in 235 ml of acetonitrile and 231 ml of purified water. Solution pH was adjusted to 7.2 with NaOH. A test paper was impregnated with this solution and dried. A second solution containing 3.50 g NaDMAB, 9.63 g NaMOPS, 6.53 g MOPS, 74 ml of 1% $Na_2EDTA \cdot 2H_2O$, and 296 ml of purified $H_2O$ was prepared. To this was added 41,700 units of horseradish peroxidase and 247 mg of ascorbic acid. pH was adjusted to 7.20 with concentrated HCl and NaOH. To this solution was then added 138,000 units of alcohol oxidase (as solution—Phillips). The solution was stirred until uniform and applied to the test paper to saturation and then dried to yield a final ethanol test paper which gave superior results determining ethanol in aqueous media. This material was affixed to a polystyrene backing by a solvent fusion technique wherein the polystyrene was softened with toluene and the paper adhered to it to give a test device.

What is claimed is:

1. A method for determining the concentration of ethanol in the bloodstream of a human who is suspected of having consumed ethanol, which comprises:

(a) reacting saliva of said human with a dry, room-temperature-stable test device comprising an inert support pad containing alcohol oxidase, mannitol present in an amount sufficient to stabilize the alcohol oxidase, a salt that buffers in the range of pH 6-9, a substance having peroxidase activity, and a substance which will react with hydrogen peroxide to give a compound of changed color, whereby a change of color is obtained in the presence of ethanol; and (b) comparing any color so obtained to a standard to determine the ethanol concentration in the bloodstream of said human.

2. The method of claim 1, wherein said test device further comprises a polyamine polyacid metal chelating agent.

3. The method of claim 1, wherein said test device comprises alcohol oxidase in intimate admixture with from 300-2500 mg of said mannitol per 1000 enzyme units of alcohol oxidase.

4. The method of claim 3, wherein said test device further comprises from 2-50 mg of a polyamine polyacid metal chelating agent per 1000 enzyme units of alcohol oxidase.

* * * * *